(12) United States Patent
Sharma

(10) Patent No.: US 12,083,041 B2
(45) Date of Patent: Sep. 10, 2024

(54) INTRAOCULAR DEVICES AND METHODS

(71) Applicant: Anant Sharma, Bedfordshire (GB)

(72) Inventor: Anant Sharma, Bedfordshire (GB)

(*) Notice: Subject to any disclaimer, the term of this patent is extended or adjusted under 35 U.S.C. 154(b) by 823 days.

(21) Appl. No.: 16/499,437

(22) PCT Filed: Mar. 28, 2018

(86) PCT No.: PCT/GB2018/050806
§ 371 (c)(1),
(2) Date: Sep. 30, 2019

(87) PCT Pub. No.: WO2018/178658
PCT Pub. Date: Oct. 4, 2018

(65) Prior Publication Data
US 2021/0100686 A1 Apr. 8, 2021

(30) Foreign Application Priority Data
Mar. 31, 2017 (GB) .................. 1705177

(51) Int. Cl.
*A61F 9/00* (2006.01)
*A61F 9/007* (2006.01)

(52) U.S. Cl.
CPC ........ *A61F 9/0017* (2013.01); *A61F 9/00745* (2013.01); *A61F 9/00781* (2013.01); *A61B 2217/005* (2013.01); *A61B 2217/007* (2013.01)

(58) Field of Classification Search
CPC .. A61F 9/008; A61F 9/00736; A61F 9/00781; A61M 27/002
See application file for complete search history.

(56) References Cited

U.S. PATENT DOCUMENTS

| 5,041,081 A | 8/1991 | Odrich | |
| 5,178,604 A * | 1/1993 | Baerveldt | A61M 27/002 604/9 |
| 5,704,907 A * | 1/1998 | Nordquist | A61F 9/00781 604/8 |
| 5,743,868 A * | 4/1998 | Brown | A61F 9/00781 604/9 |
| 5,817,099 A | 10/1998 | Skolik et al. | |
| 6,186,974 B1 * | 2/2001 | Allan | A61F 9/00781 604/30 |
| 6,544,208 B2 * | 4/2003 | Ethier | A61F 9/00781 137/844 |
| 6,881,198 B2 * | 4/2005 | Brown | A61F 9/00781 604/9 |

(Continued)

FOREIGN PATENT DOCUMENTS

WO 2012/040380 A1 3/2012
WO 2014/190029 A1 11/2014

OTHER PUBLICATIONS

Khng, Christopher et al., "Intraocular pressure during phacoemulsification", J Cataract Refract Surg. 2006; 32(2):301-8, Feb. 2006, 8 pages.

(Continued)

*Primary Examiner* — Scott J Medway
(74) *Attorney, Agent, or Firm* — Weber Rosselli & Cannon LLP

(57) ABSTRACT

The present application relates to novel intraocular devices and their use in surgical techniques, as well as the novel surgical methodology achieved from their use.

18 Claims, 4 Drawing Sheets

(56) References Cited

U.S. PATENT DOCUMENTS

| | | | | |
|---|---|---|---|---|
| 7,867,186 | B2* | 1/2011 | Haffner | A61F 9/00781 606/108 |
| 9,603,742 | B2* | 3/2017 | Sanchez | A61F 9/00781 |
| 10,201,451 | B2* | 2/2019 | Camras | A61F 9/00781 |
| 10,271,989 | B2* | 4/2019 | Haffner | A61F 9/0017 |
| 10,980,667 | B2* | 4/2021 | Brown | A61L 31/06 |
| 11,116,625 | B2* | 9/2021 | Kalina, Jr. | A61F 2/1664 |
| 2002/0007150 | A1* | 1/2002 | Johnson | A61F 9/00745 604/294 |
| 2011/0028884 | A1* | 2/2011 | Theodore Coroneo | A61F 9/00781 606/6 |
| 2012/0220917 | A1* | 8/2012 | Silvestrini | A61F 9/00781 604/8 |
| 2013/0274788 | A1* | 10/2013 | Jennings | A61B 17/0231 606/191 |
| 2015/0148729 | A1* | 5/2015 | Pinchuk | A61M 27/002 604/8 |
| 2016/0081852 | A1* | 3/2016 | Peyman | A61F 9/00827 604/20 |
| 2020/0306086 | A1* | 10/2020 | da Silva Curiel | A61F 9/00781 |

OTHER PUBLICATIONS

Tranos, Paris G. et al., "Same-day versus first-day review of intraocular pressure after uneventful phacoemulsification", J Cataract Refract Surg—vol. 29, Mar. 2003, 5 pages.

Ng, David T. et al., "Intraoperative complications of 1000 phacoemulsification procedures: A prospective study", J Cataract Refract Surg. Oct. 1998; 24(10):1390-5, 6 pages.

Kass, Michael A. et al., "Delaying Treatment of Ocular Hypertension: The Ocular Hypertension Treatment Study", Arch Ophthalmol 128 (3), 276-287, Mar. 2010, 12 pages.

Zhao, Yune et al., "Intraocular Pressure and Calculated Diastolic Ocular Perfusion Pressure during Three Simulated Steps of Phacoemulsification In Vivo", IOVS, Jun. 2009, vol. 50, No. 6. pp. 2927-2931, 5 pages.

International Search Report and Written Opinion issued on Aug. 30, 2018 in corresponding International Application No. PCT/GB2018/050806; 21 pages.

* cited by examiner

INTRAOCULAR DEVICES AND METHODS

FIELD

The present application relates to novel intraocular devices and their uses in surgical techniques, as well as the surgical methods that result from their use.

BACKGROUND

A cataract is a clouding of the lens inside the eye, causing vision loss that cannot be corrected without surgery. Cataracts are predominantly associated with the natural aging process and due to the increasing aged population globally, the prevalence of cataracts is expected to continue to grow significantly. Over 300,000 cataract operations are done per year in the UK alone. It is therefore desirable to provide safe, effective and efficient means for removal of the clouded lens (and replacement with an artificial intraocular lens IOL) to restore clear vision to patients.

De-risking the steps in cataract removal and techniques performed in other delicate eye surgeries are crucial to advancing this surgical field. Improvements, in cataract surgery particularly, are both technically challenging and commercially valuable; some severe complications, such as central visual loss following cataract surgery are not yet fully evaluated. Thus, understanding and controlling those factors which play a part in complications of this type of surgery remain of considerable interest.

Typically, a modern cataract removal procedure utilises a high-frequency ultrasound device that breaks up the cloudy lens into pieces; these are then gently removed from the eye by suction. Such a procedure is called phacoemulsification and can be performed with only relatively small incisions, which is beneficial for healing.

Most phacoemulsification involves a main incision of 2.0 mm-2.4 mm with either one or two smaller incisions for second instrument such as irrigation and aspiration apparatus. Another particular technique, known as bimanual micro-incision phacoemulsification, involves cataract extraction via two incisions of less than 1.5 mm diameter. Surgeons in the field consider that intraocular lenses capable of insertion through such dimensions will soon become widely available and hence this technique will grow in popularity; from a surgeon's point of view, such a surgical step is more advanced, offering improved anterior chamber stability and access to the capsular bag.

Hydrodissection is an essential step during the phacoemulsification procedure because it allows separation of the cortex from the capsule of the eye. The spatial separation facilitates easier and more complete cortical removal with less stress on the zonules; the rings of fibrous strands that connect the ciliary body with the crystalline lens of the eye. Hydrodissection also allows nuclear mobility to aid fragmentation of the cataract.

However, this step is still regarded by experienced ophthalmic surgeons as remaining an uncontrolled manoeuvre because during the hydrodissection stage particularly, it has been noted that the intraocular pressure (IOP) is often raised to a relatively high level (Khng C, Packer M, Fine I H, Hoffman R S, Moreira F B. Intraocular pressure during phacoemulsification. J Cataract Refract Surg. 2006; 32(2):301-8.). This situation may be exacerbated because the cannula being used to conduct the surgery in micro-incision phacoemulsification occupies a small diameter as compared to the incision wound and fluid readily moves out of the surgical wound in an uncontrolled manner. On some occasions, the iris of the eye will be pulled through the incision, causing an iris prolapse.

This surgical step therefore gives much cause for concern to surgeons as it routinely involves an uncontrolled risk factor resulting in one or more surgical complications.

http://webeye.ophth.uiowa.edu/eyeforum/tutorials/iris-prolapse-history.htm (accessed September 2017).

Of particular concern is eye structure prolapse, particularly iris prolapse. This type of trauma is reported between 0.5% and 0.6% of all cataract surgeries (Ng D T, Rowe N A, Francis I C, et al. Intraoperative complications of 1000 phacoemulsification procedures: a prospective study. J Cataract Refract Surg. 1998; 24(10):1390-5.). Minor prolapses are often not reported.

Complications, such as iris prolapse, are more likely to occur in small pupils, Intra operative floppy iris syndrome (IFIS), shallow anterior chambers and small eyes. In particular diabetes, age, drugs, such as pilocarpine, previous surgery and inflammation are some of the contributing factors in a small pupil. It is further known that patients using certain drugs, for example, Tamsulosin, to treat prostate hypertrophy may also contribute to IFIS.

Techniques to reduce complications in these cases have been suggested in the art. However, they typically result in additional operative difficulty/risk and/or may not be suitable for certain groups of patient. For example, longer wound tunnels (incisions) make operative visualization challenging for the surgeon and risk increased astigmatism. Such long tunnel incisions may also not be possible in patients with previous corneal surgery or pathology.

It has been difficult for surgeons to identify/utilise suitable instruments during phacoemulsification that overcome this problem. Currently eye surgery is carried out in closed systems with a pump, e.g. peristaltic pump, which controls the exit and entry of fluid into the wound site. There can be insufficient irrigation in-flow which then further reduces anterior chamber stability. Such systems maintain an inflated eye shape to allow a workable surgical site during the procedure (to achieve this sometimes the bottle height is elevated but such action likely contributes to a raised IOP). Previously, surgeons have attempted to use pressurized irrigation to maximize inflow. However, increased inflow pressure also carries risk for elevated IOP if outflow from the eye ceases, even transiently.

Rises in IOP, even after the hydrodissection step, continue to present a problem for some patients and therefore mitigating such a risk is challenging for surgeons. IOP has been shown to rise significantly throughout cataract surgery (Yune Zhao, Xingyu Li, Aizhu Tao, Jianhua Wang, and Fan Lu Intraocular Pressure and Calculated Diastolic Ocular Perfusion Pressure during Three Simulated Steps of Phacoemulsification In Vivo. IOVS, June 2009, Vol. 50, No. 6. Pages 2927-31) and it can cause damage to the eye, especially in patients with glaucomatous optic nerve damage, a condition which is more sensitive to IOP rise. For example, insertion of the intraocular lens toward the end of the cataract surgery is also a surgical step which significantly raises the IOP.

Finally, IOP rise can also occur after cataract and other eye operations such as glaucoma filtration procedures (trabeculectomy, tube drainage surgery), corneal transplant surgery, cellular transplant surgery, retinal and/or vitreous surgery. This is known to damage the optic nerve with wipe-out of the visual field and central vision and other complications such as permanently dilated pupil, corneal oedema (swelling) with visual loss. In high risk cases medication such as diamox tablets or eye drops is given to reduce IOP, however the IOP can still rise (Kass M A, Gordon M O, Gao F et al. (2010). Delaying Treatment of Ocular Hypertension: The Ocular Hypertension Treatment Study. Arch Ophthalmol 128 (3), 276-287).

IOP has also been known to rise post-surgery in normal patients and cause damage such as reduced vision, dilated pupil and loss of visual field. IOP rises after cataract surgery is remains an important and common problem since IOP rise can exacerbate vision loss particularly in glaucoma patients who have pre-existing visual field defects (Tranos et al., 2014).

It is therefore considered that in the field of ocular surgery there is a need for improvements in techniques and apparatus to manage or reduce the risk associated with uncontrolled steps of that surgery.

In particular, in modern day cataract surgery there is a clear need for new procedures, techniques and surgical tools to reduce the risk of operative and post-operative complications. This is especially true as it concerns modern phacoemulsification to prevent iris prolapse and other significant complications associated with a rise in IOP, whether occurring during surgery or post operatively.

The present invention arises from a desire by the applicant to address the technical issues associated with the risks of ocular surgery, as described above.

SUMMARY

The present invention concerns a device for use in ocular surgery and/or post-operative surgical care comprising a solid core structure adapted to form a peripheral seal with an ocular layer(s) about the device in-situ, the structure comprising at least one internal channel adapted to balance intraocular pressure by permitting at least one of a fluid or gas to pass through the structure.

Such a device may be safely placed and/or secured past the pupil margin, for example, during cataract surgery. However, for other types of surgery, the device may be placed elsewhere in the eye, including the cornea, limbus, sclera, suprachoroidal space, or in the layers of the conjunctiva, such as subconjunctival or subtenon.

Techniques/manoeuvres such as hydro-dissection, as described during cataract removal, can be carried then out by the surgeon with reduced risk of complication.

For example, after placing the device and initiating hydro-dissection, any excess fluid in the eye may safely move from an internal chamber, at the working surgical site of the cataract, towards a distal end of the device and will flow via the internal channel of the core structure and out the proximal end, which is external of the corneal outer layer. Essentially, the presence of the device in the eye therefore prevents the build-up of unwanted IOP. Further, the device enables the pressure to be balanced or a build-up to be passively neutralised without requiring any external pumping action.

In particular, the device of the invention allows the surgeon to continue to undertake a surgical procedure in the eye with reduced concern about uncontrolled change in IOP. Further, this removes the need to take urgent steps to rectify, if possible, complications that result, such as an enhanced risk that essential eye structures, such as the iris are dragged out of the eye.

The solid core may be adapted to form such a seal by, for example, being compressible, deformable or otherwise malleable to ensure the device can be inserted easily through an incision but remain fitted to the ocular layer(s) through which it passes. In preferred embodiments the core structure of the device may be circular or ellipsoid in cross-section.

The core structure of the device typically comprises a proximal end (proximal to the user/surgeon) and a distal end.

In embodiments, the device may range from 0.01 mm to 50 mm in length, that is, the measurement between the two ends of the device. In some embodiments the structure is elongate and hence shaped like a tube or sleeve-like.

The core structure of the device may further comprise a retaining feature to help prevent the device from becoming displaced. The retaining feature may be a corrugated outer surface for enhanced grip with the ocular layer(s). In other embodiments the elongate structure may have a screw thread configuration to allow to the device to be more securely fixed in the eye.

In further embodiments, the core structure may additionally or alternatively have a retaining structure with an outer surface comprising angled protrusions, in the form of a plurality of feet, flaps or wings, evenly spaced in a circumferential manner or a single angled annular flap which may permit the device to be inserted though the cornea, or other structure of the eye, and which may temporarily retain the device in the inserted position thereafter by resting against an inner domed surface of that structure, such as the cornea.

Typically, the device of the invention may have an average width or cross section ranging from 0.001 mm to 15 mm in size.

The diameter (or size of cross section) at the proximal end may be the same or different to the distal end. In some embodiments the cross section of the structure is constant.

In other embodiments the cross section of the structure may vary, or have a sliding gradient. For example, the device may taper toward the distal end, whereby the cross section of the distal end is narrow as compared to the cross section at the proximal end. In such embodiments the tapered end permits ease of entry when inserting the device into the eye. Such a configuration may allow the surgeon to make the incision with the device itself, hence dispensing for the need of an additionally pre-made incision with a different tool. The edge of the distal end of the device maybe further shaped to facilitate penetration through the layer(s) of the eye. In some cases the distal end maybe round-ended with side ports, in other examples the distal end may be bevelled, chiseled or sharp to enhance the ease of placement.

In some embodiments the structure of the device comprises walls which range from 0.0001 mm to 5 mm in thickness.

The device may preferably be formed from an elasticated material to enable the surgeon to easily place the device within a very small incision in the eye and therefore permit the peripheral seal to be tight with the ocular layer(s). The device may be formed from a material biocompatible with ocular tissue such as plastics or silicone, including grade a silicone. Such materials include but are not limited to medical grade silicone, silicone polymer, silicone rubber, rubber, latex, Teflon, polypropylene, nylon, plastic and thermoplastic polyurethanes.

In some embodiments the structure of the device comprises a plurality of internal channels. Said multiplicity of channels can serve to provide optimal irrigation and balancing of IOP functioning to promote effective drainage. The one or more further internal channels may provide different functionality, so the device is adapted to permit efficient release of gas or fluids of differing viscosity, in addition to the removal of excess physiological fluid, such as balanced salt solution, isotonic saline or viscoelastic fluid such as sodium hyaluronate, hypromellose.

The device may further comprise further features to enhance or promote movement of physiological or non-physiological fluid out of the eye when IOP is raised. In some embodiments the movement is promoted by a feature positioned within the internal channel, such as grooves or valves. In some embodiments, the movement of the fluid is able to be controlled by one or more of those valves, for example by one-way valves. In other embodiments the valve are pressure valves. In embodiments the pressure values are pre-set such that when pressure exceeds the setting the valve will open to allow the fluid to escape the proximal end of the structure of the device. Such pressure valves allow a closed system to be retained as far as possible without risking uncontrolled rises in IOP. Such a pressure valve may be positioned within the internal channel of the core structure.

In some further examples of the invention, the structure of the device may comprise an annular flange at the proximal end of the core structure which may sit on the surface of the eye structure, such as the cornea. This feature allows the maximum depth of the device during insertion into the eye structure to be pre-determined and thus controlled when the length of the core structure is known. It prevents the device from being embedded too deeply in the eye and also facilitates insertion and removal.

The device of the invention may be used in situ, temporarily, during surgery and removed once the surgical procedure is complete. In such embodiments the device is therefore removable and may comprise features described herein to further facilitate that removal.

However, the device may instead form a permanent seal with the layers of the eye and thus either remain embedded therein permanently, or until it naturally dissolves. In such embodiments, the device may be made from a biodegradable or non-biodegradable material.

In examples relating to post-surgical or non-surgical associated treatment of IOP, where it is intended to install the device for post-surgical care, or leave the device in position thereafter, the device may be made of a dissolvable material. The material of the device, once in situ, is biodegradable and dissolves to close the wound within 6 weeks of insertion. Such an embodiment helps ensure safe wound closure whilst continuing to keep the IOP balanced for a minimum period of time post surgery. This is especially useful where IOP continues to be a high risk factor post-surgery, for example in certain patient groups e.g. glaucoma. Alternatively, the non-biodegradable embodiment of the device can simply be removed after a minimum period of time.

There is further disclosed, a kit comprising a plurality of ocular devices according to any of the before described embodiments, wherein at least two of the devices accord to different embodiments of the invention as herein before described. It is considered that the invention may be provided as a kit to the surgeon so he/she may select the appropriate device according to the surgical need. For example, a patient with a particular risk or with smaller eyes may require a differently sized device. It is therefore valuable that the surgeon has a choice of appropriate devices from which he may choose each having the essential feature of the invention.

Furthermore, in another aspect the invention concerns a surgical apparatus including for example a hydrodissection device or a lens injection device, for use in ocular surgery comprising: an elongate cannula shaft for the introduction of fluid or gas into an ocular space and a hollow annular, flexible, sleeve surround, wherein the sleeve comprises a plurality of apertures to permit excess fluid or liquid in the ocular space to re-enter the device to exit the ocular space thereby balancing intraocular pressure during surgery.

In this aspect of the invention the device provides both the function of introducing the fluid necessary for hydrodissection and still solves the technical problem but does so in a slightly different way. Here the excess fluid, whether physiological fluid and/or other fluids needed in the procedure such as viscoelastic solution used during introduction of the new lens into the eye.

The invention of the applicant extends to a basic solid (preferably compressible or flexible) device in accordance with the many embodiments hereinbefore described may be utilised with a normal hydrodissection cannula or lens injector. For example, in such embodiments, the device forms the "sleeve surround" and necessarily includes a series of apertures provided therein. In such embodiments the device is therefore temporary or removable and may be selected to retro-fit an existing cannula to create a hydro-dissection device for use during surgery. The removable device may be disposable after use with the cannula in this form or in some embodiments it may be possible detach the cannula from the device but leave the basic device in the eye thereafter for post-surgical maintenance.

In another aspect the invention relates to use of the device or the surgical apparatus incorporating the device of the invention, or any embodiment thereof, in ocular surgery. In a further aspect the invention relates to use of the device or the surgical apparatus in cataract surgery. In another aspect the invention relates to use of the device or surgical apparatus, in any embodiment described, in phacoemulsification surgery.

In a further aspect the invention relates to use of the device, or the surgical apparatus incorporating the device as described herein, in a hydro-dissection or other step of phacoemulsification surgery, angle surgery such as schlemm canal or trabecular surgery including stents, implants or vitreoretinal surgery.

In another aspect the invention concerns use of device for post-surgical maintenance of intraocular pressure in the range of 3<30 mmHg.

In another aspect the invention relates to a method of controlling intraocular pressure during surgery to the eye comprising inserting the device or surgical apparatus incorporating the device according to any embodiment of the invention.

In a further aspect the invention concerns a method of maintaining an intraocular pressure in the range of 3 to <30 mmHg during surgery to the eye comprising inserting the device or surgical apparatus according to any embodiments described.

In particular, the present invention further concerns a method of surgical cataract removal comprising the steps of: viscoelastic insertion, capsulorhexis, hydrodissection; intraocular lens insertion; phacoemulsification; irrigation; lens aspiration and viscoelastic fluid removal, wherein during one or more of the above steps the device or surgical apparatus, as previously described, is used to balance intraocular pressure throughout the removal.

An uncontrolled change in IOP, described in the before-mentioned background to the invention is associated with a number of complications and risk factors during surgery to the eye. Therefore, maintaining a safe IOP during any eye surgery technique or step in which IOP is characteristically a risk factor is beneficial to the patient and to the surgeon since it prevents an uncontrolled factor effecting the flow, efficiency and precision of the procedure as a whole. The benefit of the invention however has been found particularly beneficial in cataract removal and specifically procedures that require hydrodissection.

BRIEF DESCRIPTION OF THE FIGURES

Various features, embodiments and examples of the presently disclosed invention including the device, methods will now be described herein with reference to the accompanying figures wherein.

DETAILED DESCRIPTION

As used herein, the term "proximal" refers to the end of the apparatus or feature which is closer to the user or clinician and the term "distal" refers to the end of the apparatus which is relatively speaking distanced from the user as compared to the proximal end.

Variations of the presently disclosed device are possible and within the scope of the present disclosure provided the major features of the invention are present, as defined by the claims.

Figure 1:
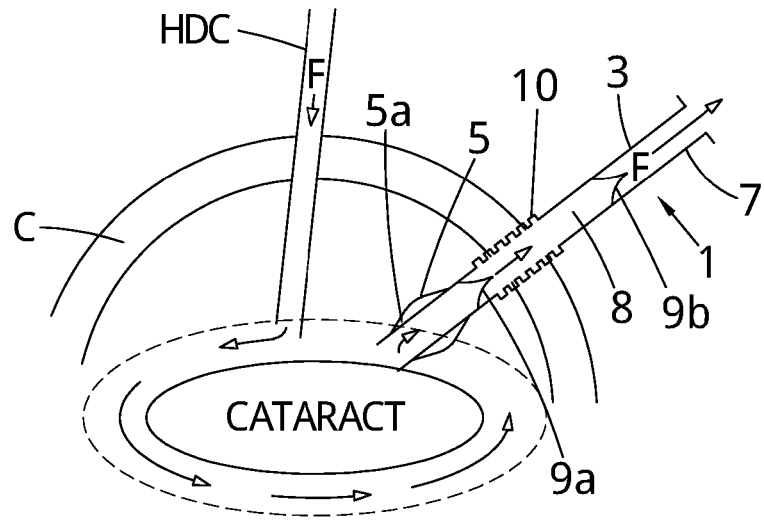
FIG. 1 illustrates a first aspect of the device of invention positioned relative to the structure of the eye.

In FIG. 1 the device of the invention is shown in-vivo as would be seen according to a rough cross-section of the structure of the eye. In this embodiment the device is positioned during ocular surgery, in particular during a cataract removal procedure, for example. However, the device in any of the examples described, wherein it is not permanently part of a larger surgical device such as a hydro-dissector or lens injector, could equally remain in place postoperatively. Alternatively, the device shown could be inserted purely for IOP care or maintenance, in order to obtain the effect, without having been directly used during formal surgery, per se.

During hydrodissection step of cataract removal, the surgeon must insert a hydrodissection cannula HDC through the cornea, as shown in the figure. After capsulorhexis, the device 1 of the invention will be inserted at different location.

The device 1 has a deformable core, or central structure, shown as section 3. When inserted in to the eye, the core compresses and its external surface adapts with the ocular structure surface such as the cornea C, through which it is passed, forming a peripheral seal therewith. The core structure has a distal end 5 and a proximal end 7, with an internal channel 8 extending there through. The device is a compressible or deformable material to enable a very small incision in the eye and yet permit the peripheral seal to be tight. The device may be formed from one or more functional material biocompatible with ocular tissue such as flexible plastic or silicone. In preferred examples, such as this, the device is formed from any material, or materials in combination, conforming to European and International regulatory requirements for surgical devices and implants.

The surgeon may make a micro incision (currently 0.5-3 mm in cataract surgery) in order to apply the device to the position shown in FIG. 1. However, the device may have features to allow for self-insertion without the need for a pre-incision. For example, in some examples or embodiments the distal end 5 may be bevelled or pointed such that the device facilitates self-insertion. In some examples, the distal end 5 may alternatively or additionally be made of a slightly harder material 5*a* to enable insertion with the device alone.

In the example shown, the core structure 3 with a substantially circular cross-section and the device is generally elongate with a tube or sleeve-like shape. Importantly, the selection of a particular measurement combination may be made such that the device is suitable in view of a patient's eye shape and dimension. The width or cross-section dimension of the device is typically in the range of 0.001 mm to 15 mm in size, whereas the length may range from 0.01 mm to 50 mm. The surgeon may therefore select an embodiment of the device, corresponding to a combination of the ranges, herein described, to provide a suitable patient match, especially if the device is intended to remain in the patient's eye post-surgery or inserted independently into the eye. In this regard, an embodiment of the invention concerns a provision of a device kit in which a selection of the most common combination is provided for in one useful pack.

In the example shown, the diameter of the core structure is generally constant. In this example, the core structure also comprises a corrugated section 10 (but it may be corrugated throughout). The corrugated outer surface of the structure of the device enhances grip with the corneal layer(s) and after insertion helps prevent the device from becoming displaced (during the rest of the procedure) since the structure (due to the internal pressures) may be liable to slip from the original position in a proximal direction.

Once the device is safely placed and/or secured past the pupil margin hydro-dissection may proceed. On initiating hydrodissection, any excess fluid introduced into the eye by the in the eye may safely move from the internally closed chamber at the working surgical site of the cataract towards the distal end of the device and flows (shown by the directional arrows and F) via the internal channel out the proximal end. The device therefore prevents the build-up of unwanted IOP and the full procedure of cataract removal can be carried out with reduced risk of complication that is associated with unbalanced IOP. Furthermore, since the device provides a secure seal, the eye remains expanded and does not collapse even once excess fluid has escaped from the surgical site.

As shown herein, the device enhances or promotes movement of physiological fluid out of the eye when IOP is raised. This movement is further promoted by at least one valve 9 positioned within the internal channel of the core structure; here two valves 9*a*, 9*b* are shown to regulate the movement of fluid more precisely. Such valves include one-way valves, for example. In particular, the movement of the fluid is able to be controlled and the IOP balanced even more precisely when multiple valves within the internal channel 8, in this example two, are positioned either side of the corneal wall.

Figure 2:
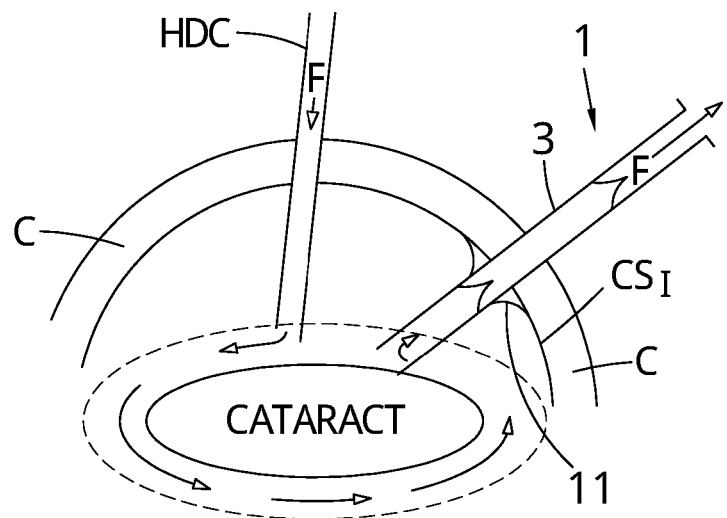
FIG. 2 illustrates an embodiment of the invention.

A further embodiment of the device is provided in FIG. 2. Here the device of the invention is similarly constructed in its main elements as before described in FIG. 1. However, the retaining structure which secures the core structure in this example is a stabiliser 11 comprising an outer surface angled protrusion or protrusions, for example in the form of a plurality of feet, flaps or wings evenly spaced in a circumferential manner or a single angled annular flap. The stabiliser permits the device to be inserted though the cornea in the manner previously described but will act to temporarily retain the device in the inserted position specifically by resting against an inner concaved surface CSI of the cornea incision layer. The device may be retained against other layers of the eye, e.g. sclera, choroid, parsplana.

During glaucoma or combined glaucoma/cataract surgery, the device therefore acts as IOP balance mechanism but also, crucially, postoperatively functions to allow the eye to inflate if over drainage occurs.

Figure 3A:
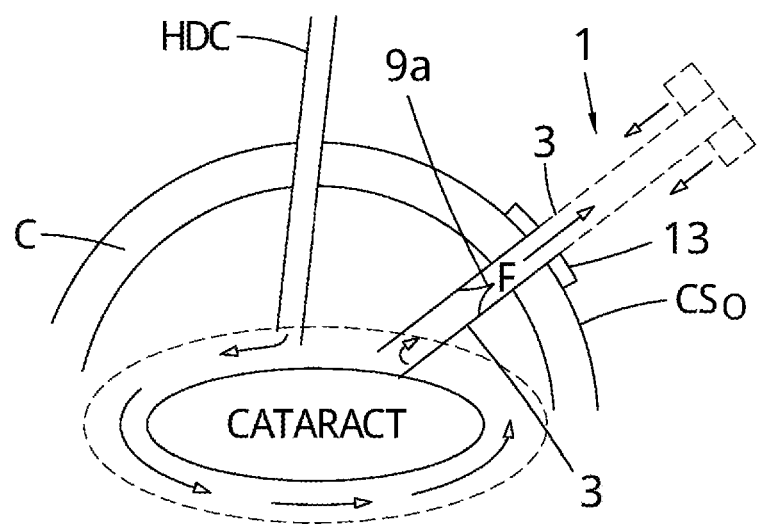
FIG. 3A illustrates a further embodiment of the device of the invention.

FIG. 3A provides a further embodiment in which different types of valve may be used together to provide enhanced control of fluid movement and ease of use. In this embodiment, the device of the invention comprises an annular flange or lip 13 at the proximal end of the core structure which may sit of the surface of the cornea once the device is inserted. During insertion this feature stops the device (at the proximal end) from penetrating the cornea past beyond a maximum depth (which is pre-determined as the length of the core structure in relation to the flange is known) and lies upon an outer convex surface of the cornea CSO. The flange therefore facilitates both insertion and removal of the device. This configuration helps control and distance the device, when in situ, from the posterior surface of the cornea, especially in eyes with shallow anterior chambers thereby avoiding potential injury. In an additional embodiment the flange maybe adjustable along and temporarily fixed in place on the compressible structure 3 such the proximal end of the device protrudes therefrom (shown in dash).

Figure 3B:
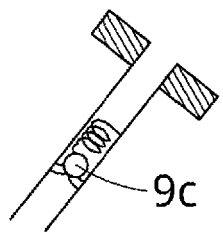
FIG. 3B illustrates a number of further embodiments of the device.

The device in another embodiment, shown in FIG. 3B, may instead comprise an internal valve, in this case a spring-based valve 9c, which can be pre-set to function under particular pressure ranges. However, other valves such as more simplistic flap valves and one-way valves, such as 9a, may equally be utilised in this combination. Alternatively, such valves can be electronic and/or magnetic and control valve pressure such that they may be adjusted when device is in situ.

In addition to that configuration, in other examples, the flange may also function as a pressure valve by temporarily sealing the proximal end of the device. The flange is adapted to deform under pressure from fluid in the internal channel to create a temporary aperture at the proximal end of the device when the IOP rises and fluid moves into the internal channel.

In any case, a pressure value can pre-set such that when pressure exceeds the setting in the internal channel the valve will open to allow the fluid to escape the proximal end of the structure of the device. In particular, pre-set pressure valves allow a closed system to be retained as far as possible without risking uncontrolled rises in IOP and only one valve need be utilised for this function although they may be used in combination.

Figure 4:
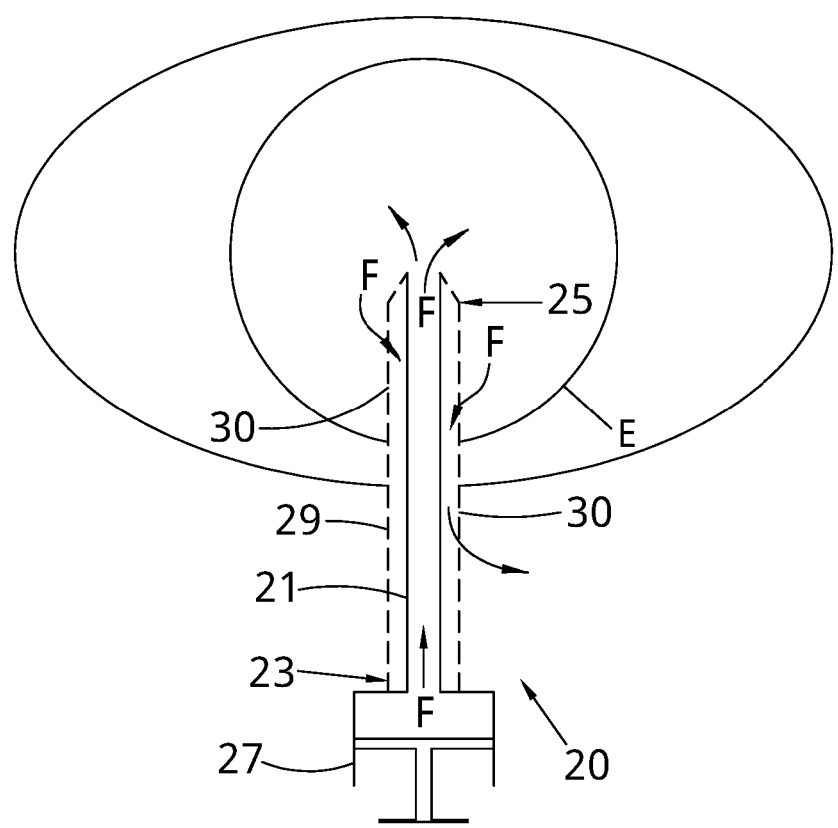
FIG. 4; illustrates a further aspect of the invention in which a surgical apparatus such as a hydrodissector incorporates a device.

FIG. 4 shows a hydrodissection device 20 with proximal and distal ends, 23 and 25 in accordance with a further aspect of the present invention. Such a device comprises a central shaft 21. The device typically comprises a fluid injection means or apparatus 27 at the proximal end 23 of the device for inserting fluid into the ocular space during surgery. The device further includes a hollow annular flexible sleeve surround 29, wherein the sleeve comprises a plurality of apertures 30 spaced there along to permit excess fluid or liquid in the ocular space to re-enter the device to exit the ocular space thereby balancing intraocular pressure during surgery. A simplistic illustration of the movement of fluid F is shown by arrows when the device is utilised in surgery of the eye E.

The invention of the applicant also covers the embodiment in which a basic compressible device in accordance with the many embodiments hereinbefore described as 1 may be utilised with a central shaft hydrodissector, for example, as the "flexible sleeve surround" 29 when the compressible device 1 necessarily includes a series of apertures therein (shown as 30 in the present embodiment). In such embodiments the sleeve/basic device may be selected to retro-fit the desired cannula to create a hydrodissection device. The sleeve may therefore be disposable after use with the cannula in this form. The hydrodissection sleeve cannula can be attached/detached to the syringe.

The device in combination therefore usefully provides both the function of introducing the fluid necessary for hydrodissection step of surgery and still solves the technical problem relating to IOP build up, but does so in a slightly different way since such a device when used with a cannula necessarily requires apertures along, whereas when used alone this feature must not be included.

Figure 5:
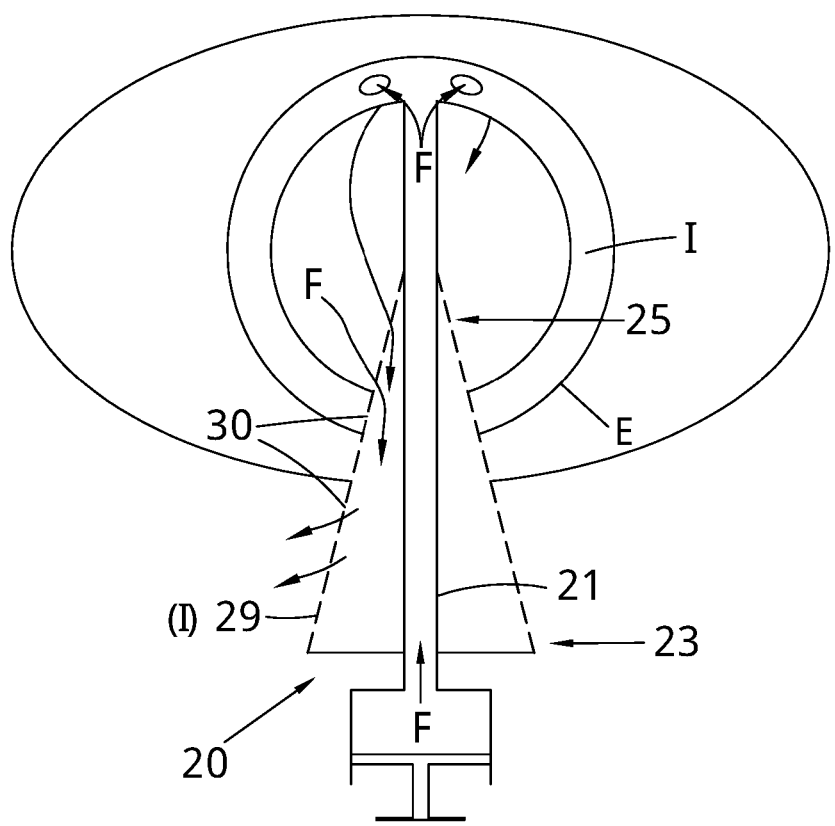
FIG. 5; illustrates embodiments in which device of the invention when used in combination with an instrument of surgery is either removable or integrated with an instrument used in ocular surgery.

In other embodiments, as shown in FIG. 5, the removable/adjustable compressible device 1 is either used with an instrument such as a cannula, or wherein the sleeve 29 is integrated with the cannula of a hydrodissection device for example. In such embodiments, the cross-section of the sleeve surround has a sliding gradient; the device 1/sleeve 29 taper towards the distal end, whereby the cross section of the distal end 25 is narrow as compared to the cross section at the proximal end 23. In such embodiments the tapered end permits ease of entry when inserting the device into the eye. Such a configuration may in particular allow the surgeon to make a micro incision with the device itself, hence dispensing for the need of an additionally pre-made incision with a different tool. The edge of the distal end of the device may further be bevelled, chiseled or sharp to enhance the ease of placement. By virtue of the tapering of the sleeve, a peripheral seal with the eye is formed allowing for an improved device.

During use of the surgical apparatus, the fluid F flows down the shaft 21 of the cannula and into the eye, where after, excess fluid F is enabled to return from under the iris I back into the device via the apertures 30 in the removable device 1 or sleeve 29 thereby escaping the ocular space, avoiding IOP from rising.

In other embodiments the excess fluid/gas may include more than one physiological/non-physiological fluid or gas. For example, viscoelastic fluid is needed in the procedure during introduction of a new lens into the eye. A lens injector filled with such fluid and a lens and injected in a closed system necessarily raises the pressure in the eye further. However, the invention is equally useful here; this additional fluid may also be safely removed by the same mechanism. In particular, the device can be placed temporarily through paracentesis when lens is being inserted to allow viscoelastic and/or other liquid already present in the ocular space to escape safely via the device 1 or sleeve 29, rather than increase the IOP beyond 30 mmHg, thereby potentially damaging intraocular structures, such as the zonules or capsule.

The invention claimed is:

1. A device for temporary use in cataract surgery and post-operative surgical care comprising:
   a solid core structure adapted to form a peripheral seal with one or more ocular layers, including an outer corneal layer, about the device in-situ, the solid core structure comprising a proximal end that is capable of being located externally from the outer corneal layer and a distal end and at least one internal channel connecting the ends, permitting at least one fluid to pass through the device and balance intraocular pressure, and the device further comprises at least one valve positioned within the at least one internal channel of the solid core structure which enhances or promotes movement of physiological fluid out of the proximal end and external of the outer corneal layer of the eye when the intraocular pressure is raised during cataract surgery;

wherein the solid core structure further comprises a hollow sleeve surrounding the at least one internal channel, and an outer surface of the hollow sleeve comprises a plurality of evenly spaced apertures that extend from a proximal end of the hollow sleeve to a distal end of the hollow sleeve; and wherein a cross section of the hollow sleeve gradually narrows from the proximal end of the hollow sleeve to the distal end of the hollow sleeve.

2. The device of claim 1, wherein the solid core structure is compressible, deformable or flexible.

3. The device of claim 1, wherein the device has a length in the range of 0.01 mm to 50 mm and the solid core structure is elongate.

4. The device of claim 1, wherein the solid core structure further comprises a retaining feature selected from: a corrugated outer surface, a screw thread configuration, and angled protrusions, wherein the angled protrusions are in the form of a plurality of feet, flaps or wings evenly spaced in a circumferential manner, or an angled annular flap.

5. The device of claim 1, wherein the solid core structure of the device is circular or ellipsoid in cross-section, and/or wherein the device has a cross-section ranging from 0.001 mm to 15 mm in diameter.

6. The device of claim 1, wherein a diameter of a cross-section of the solid core structure has a sliding gradient and tapers toward the distal end of the solid core structure.

7. The device of claim 1, wherein an edge of the distal end is bevelled, chiselled or sharpened.

8. The device of claim 1, wherein the device is formed from one or more materials biocompatible with ocular tissue, comprising to medical grade silicone, silicone polymer, silicone rubber, rubber, latex, Teflon, polypropylene, nylon, plastic, thermoplastic polyurethanes and biodegradable dissolvable material.

9. The device of claim 1, wherein the solid core structure of the device comprises an annular flange at the proximal end of the solid core structure.

10. The device of claim 1, wherein the solid core structure of the device comprises a plurality of internal channels.

11. The device of claim 1, wherein the at least one internal channel of the device is a single internal channel, the single internal channel further comprises one or more grooves or a plurality of valves comprising one-way, pre-set and/or pressure valves.

12. The device of claim 1, configured to be a removable attachment with a shaft of an ocular surgical apparatus, wherein the at least one internal channel of the device is adapted to form a seal with the shaft.

13. The device of claim 1, wherein the device is configured for use in cataract surgery to control intraocular pressure.

14. The device of claim 1, wherein the device is configured to maintain the intraocular pressure in the range of 3 to 30 mmHg during cataract surgery.

15. A method of surgical cataract removal comprising the steps of:
hydrodissection; intraocular lens insertion; phacoemulsification; irrigation; lens aspiration and viscoelastic fluid removal, wherein during one or more of the above steps the device according to claim 1 is inserted and used to continually balance intraocular pressure throughout the surgical cataract removal.

16. The method of claim 15, wherein the device is temporarily retained in the eye after the steps are carried out.

17. The device of claim 1, wherein the cross section of the hollow sleeve gradually narrows from the proximal end of the hollow sleeve to the distal end of the hollow sleeve until a diameter of the hollow sleeve matches a minimum size required to accommodate an outer diameter of the at least one internal channel.

18. The device of claim 1, wherein an entire length of the hollow sleeve, defined from the proximal end of the hollow sleeve to the distal end of the hollow sleeve, is shorter than a length of the at least one internal channel, allowing at least a distal portion of the at least one internal channel to be exposed from the hollow sleeve.

* * * * *